United States Patent
Sater et al.

(10) Patent No.: US 7,527,637 B2
(45) Date of Patent: May 5, 2009

(54) DISTAL PROTECTION DEVICE FOR FILTERING AND OCCLUSION

(75) Inventors: Ghaleb Sater, Acton, MA (US); Allan Steingisser, Beverly, MA (US); Jonathan G. Gasson, Novato, CA (US)

(73) Assignee: Medtronic Vascular Inc., Santa Rosa, CA (US)

( * ) Notice: Subject to any disclaimer, the term of this patent is extended or adjusted under 35 U.S.C. 154(b) by 363 days.

(21) Appl. No.: 11/031,327

(22) Filed: Jan. 7, 2005

(65) Prior Publication Data

US 2006/0155322 A1 Jul. 13, 2006

(51) Int. Cl.
*A61M 29/00* (2006.01)
(52) U.S. Cl. ...................................... 606/200
(58) Field of Classification Search ................ 606/200, 606/191–194, 198; 604/96.01, 103.03; 600/1–3, 600/9, 10, 12, 13
See application file for complete search history.

(56) References Cited

U.S. PATENT DOCUMENTS

| | | | |
|---|---|---|---|
| 4,650,466 A | 3/1987 | Luther | |
| 6,074,339 A | 6/2000 | Gambale | |
| 6,187,025 B1 | 2/2001 | Machek | |
| 6,602,271 B2 | 8/2003 | Adams et al. | |
| 2002/0183783 A1* | 12/2002 | Shadduck | 606/200 |
| 2002/0188314 A1* | 12/2002 | Anderson et al. | 606/200 |
| 2003/0130682 A1* | 7/2003 | Broome et al. | 606/200 |
| 2003/0135232 A1 | 7/2003 | Douk et al. | |
| 2003/0176884 A1* | 9/2003 | Berrada et al. | 606/200 |
| 2004/0254601 A1* | 12/2004 | Eskuri | 606/200 |
| 2005/0096691 A1 | 5/2005 | Groothuis et al. | |

FOREIGN PATENT DOCUMENTS

| | | |
|---|---|---|
| WO | WO 03/020171 | 3/2003 |
| WO | WO 2004/014238 | 2/2004 |

* cited by examiner

*Primary Examiner*—Todd E Manahan
*Assistant Examiner*—Elizabeth Houston

(57) ABSTRACT

An intravascular, distal protection device including a braided mesh that may be selectively transformed between a collapsed configuration, a filter configuration and an occlusive configuration by mechanical or thermal operation. Alternatively, the distal protection device may include a non-inflatable occlusion valve located within the mesh and actuated by the same mechanical operation that transforms the braided mesh.

20 Claims, 4 Drawing Sheets

DISTAL PROTECTION DEVICE FOR FILTERING AND OCCLUSION

FIELD OF THE INVENTION

The present invention relates to distal protection devices, and specifically to filter and occluder mechanisms for use during intravascular procedures to capture potentially embolic particles.

BACKGROUND OF THE INVENTION

Diseased blood vessels are a widespread medical condition. For example, atherosclerotic plaque may develop in blood vessel walls, a thrombus (blood clot) may form in a vessel, or a stenosis may form. If a blood vessel becomes weakened, or if the accumulation of plaque or thrombi on blood vessel walls becomes too severe, surgical intervention may be required to prevent rupture or complete occlusion of the vessels. While many different surgical procedures are associated with alleviating this condition, the use of catheters is preferred, due to the minimally invasive nature of procedures involving catheters.

Many types of procedures involve the use of catheters to treat stenotic vessels or thromboses. One type of procedure is percutaneous transluminal coronary angioplasty, or PTCA, which involves the inflation of an angioplasty balloon catheter in a stenosis to dilate a coronary blood vessel. Additionally, a stent may be implanted in conjunction with this procedure to prevent restenosis, or re-narrowing of the vessel. Various other catheter-based procedures are also common, such as thrombectomy to remove a thrombus or a portion thereof or atherectomy to cut out or abrade a stenosis within a diseased portion of the vessel.

Each of these modalities is associated with a risk that particles will be dislodged during the procedure and migrate through the circulatory system to embolize, possibly causing ischaemia, infarction or stroke. To prevent patient injury from such loosened debris, clinicians may attempt to capture the potentially embolic particles using occlusion devices or embolic filters, then lysing or aspirating the entrapped particles, or removing the particles along with the filter.

Each of these embolic protection devices and methods has certain advantages and certain drawbacks. Occlusion devices will prevent all of the loosened embolic material from migrating. However, since an occluder also prevents blood flow, the duration of use of an occluder is limited. As such, occlusion is not appropriate in all cases. Further, removal of the embolic particles caught by the occluder, such as by aspiration, is an imperfect process, and some embolic particles may escape upon collapsing the occluder.

Embolic filters may be used for longer duration than occluders because filtering devices do not prevent the flow of fluid. Thus, filter devices may be used in a wider variety of procedures, although embolic filters also suffer from some drawbacks. Filters are limited in their ability to remove very small embolic particles from the bloodstream. Additionally, an embolic filter may fill up with debris sufficiently for the filter to occlude the vessel unless the filter is removed or emptied by aspiration.

Medical balloons are sometimes used to deploy implantable filters, such as vena cava filters. This type of filter is typically designed to remain in the body after deployment to serve as a prophylaxis in case a blood clot moves into the major blood vessels. Such filters are detached from the catheter during the procedure. In addition, balloons used for the deployment of this type of filter are not intended to occlude the vessel for capturing embolic particles.

A combination of filters and occluders on the same catheter has been proposed for use in heart surgery where the heart must be arrested and isolated from the rest of the cardiovascular system. One such combination filter and occluder includes a blood filtration assembly for filtering blood and a balloon occluder. However, in such devices, the filter and occluder are generally spatially separated along the shaft of a cannula such that the occluder is positioned upstream of the filter. The separation of the filter and occluder structures is often not practical for use in some procedures, for example an angioplasty procedure.

Another catheter featuring a combination of filter and occluder elements is the subject of co-pending U.S. patent application Ser. No. 10/694,944, commonly assigned to the assignee of the invention herein. In the catheters of the '944 application, a filter surrounds an inflatable occlusion balloon, which requires an elongate lumen to provide fluid communication between the balloon and an inflation/deflation system outside the patient. Such a fluid lumen may undesirably increase the overall diameter of the catheter shaft. Catheters having occlusion balloons must also be carefully designed to avoid fluid leaks, especially from the balloon itself. The '944 application also teaches an embodiment wherein a filter surrounds a non-inflatable occluder that is expandable by push-pull components in addition to those required to operate the filter.

Thus, a need exists in the art for a distal protection catheter having the perfusion benefits of a filter while also offering, selectively, the benefits of complete particle capture found in occluders. A combined embolic filter and non-inflatable occluder may satisfy such a need.

SUMMARY OF THE INVENTION

Accordingly, disclosed herein is a distal protection device that includes a combined filter and occlusion mechanism positioned at a distal end thereof. In one embodiment, a distal protection device includes a tubular shaft, a core wire and a braided tubular mesh. The core wire is slidably disposed through the shaft. The expandable mesh has a distal end that is attached about the core wire, and at least one proximal inlet opening in a wall of the mesh. The mesh is radially expandable from a collapsed configuration to a filter configuration, and is axially contractible from the filter configuration to an occlusive configuration. Transformation between the various configurations is achieved by manipulation of elongate, mechanical, push-pull components, or alternatively by thermal manipulation of shape-memory material incorporated into the mesh.

In another embodiment, a non-inflatable occlusion valve is located within the mesh to selectively seal against the inlet to block blood flow through the mesh. The occlusion valve is operated by the same elongate push-pull components that transform the mesh from a collapsed configuration to a filter configuration.

A method of using a distal protection device is also disclosed. The method includes providing a distal protection device, locating the distal protection device within a vessel, expanding a braided mesh included in the distal protection device to form a filter configuration, and axially contracting the mesh to further transform the braided mesh into an occlusive configuration. The distal protection device includes a tubular shaft having a core wire slidably disposed therethrough. The braided mesh is expandable and generally tubular. The mesh has a distal end that is attached about the core wire, at least one inlet opening in a proximal wall of the mesh, and a plurality of pores.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art based on the teachings contained herein.

BRIEF DESCRIPTION OF THE DRAWINGS/FIGURES

DETAILED DESCRIPTION OF THE INVENTION

Specific embodiments of the present invention are now described with reference to the figures, where like reference numbers indicate identical or functionally similar elements. Also in the figures, the left most digit of each reference number corresponds to the figure in which the reference number is first used. The terms distal and proximal are used herein with respect to the location of clinician. That is, proximal means close to, or in a direction towards the clinician; Distal means distant from or in a direction away from the clinician. While specific configurations and arrangements are described, it should be understood that this is done for illustrative purposes only. A person skilled in the relevant art will recognize that other configurations and arrangements can be used without departing from the spirit and scope of the invention.

Figure 1:
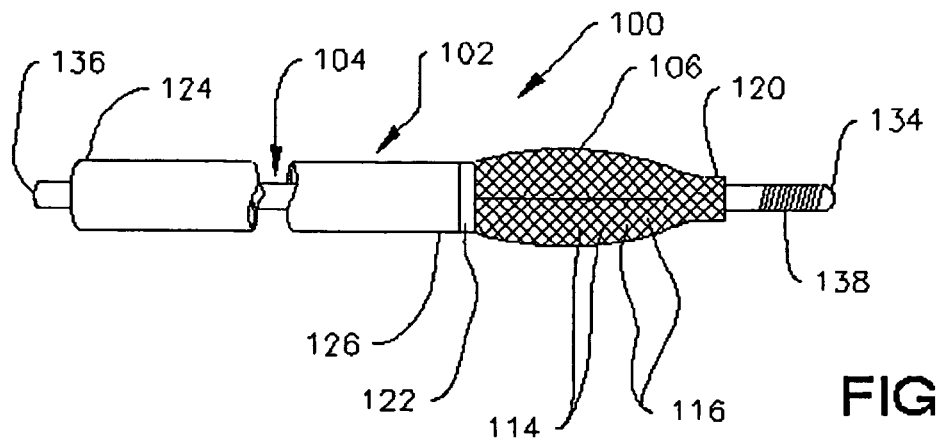
FIG. 1 is a side view of a distal protection device according to the present invention in a collapsed configuration.

Referring now to FIG. 1, distal protection device 100 according to the present invention is shown. Distal protection device 100 generally includes elongate tubular shaft 102, core wire 104 and a protection element comprising braided tubular mesh 106. Core wire 104 is a long, thin flexible wire similar to medical guidewires and core wires known in the art. Any material appropriate for use as a guidewire or core wire is appropriate for core wire 104. Such materials include stainless steel and nitinol. The dimensions of core wire 104 may be similar to guidewires and core wires used in the art, however the particular dimensions may be selected depending upon the type of procedure for which distal protection device 100 is intended. As an example, the diameter of core wire 104 is chosen so that the outer diameter of distal protection device 100 will be small enough to allow a treatment catheter to slide over it. In one embodiment, core wire 104 may have a diameter that is 0.008 to 0.009 inches. A handle, or control accessory, (not shown) may be permanently or removably attached to core wire proximal end 136 to aid a user in manipulation of core wire 104 within shaft 102.

As shown in FIG. 1, flexible tip 138 may be included on core wire distal end 134. Flexible tip 138 may act as a soft bumper to reduce potential injury to the inner walls of blood vessels. Flexible tip 138 may also be formable into an angle or "L" shape to allow distal protection device 100 to be rotatably steered through a vessel. Flexible tip 138 may be a spring or spring-like element made from the same or similar material to that of core wire 104.

Core wire 104 is slidably disposed through shaft 102. Shaft 102 is a long, hollow tube that is flexible enough to navigate the tortuous pathways of the cardiovascular system while being longitudinally incompressible enough to be pushed through the vasculature. For example, shaft 102 may be a long polymeric tube. Appropriate polymeric materials include polyethylene block amide copolymer, polyvinyl chloride, polyethylene, polyethylene terephthalate, polyamide or polyimide. Optionally, a layer of a stiffer reinforcing material may be added to or embedded within the main material of shaft 102 for a portion or the entirety thereof to enhance the longitudinal stiffness of distal protection device 100. For example, a braid of metal or polymeric filaments could be included. If made from a polymer, shaft 102 can be manufactured by any method known in the art, such as by extrusion. In addition, metals such as stainless steel, nitinol, and age hardenable Nickel-Cobalt base alloy could be used to form shaft 102, if the walls thereof are thin enough to allow shaft 102 to remain flexible. The materials and dimensions of tubular shaft 102 are selected to allow core wire 104 to slide there through. A slippery material may also be included on the outer surface of shaft 102 so that distal protection device 100 may slide more easily through a vessel. In addition, the shaft inner surface and/or the core wire outer surface may be coated with a slippery material to reduce sliding friction of core wire 104 within shaft 102.

Shaft 102 is generally shorter in length than core wire 104, although the exact lengths of core wire 104 and shaft 102 will vary depending upon the intended use of distal protection device 100. Similar to core wire 104, a handle, or control accessory may be permanently or removably attached on shaft proximal end 124. Core wire proximal end 136 extends beyond shaft proximal end 124, as both of these ends must be accessible so that each may be manipulated with respect to the other. Shaft distal end 126 terminates proximally of core wire distal end 134, and mesh 106 is located there between as discussed in further detail below.

Braided mesh 106 provides for selective filtering and occlusion in distal protection device 100. That is, manipulation of mesh 106 allows a user to selectively configure distal protection device 100 as a filter or as an occluder while the device is in situ. Mesh 106 is generally a tubular braid comprising filaments 114. The braid material of mesh 106 forms a plurality of openings, or pores 116. Mesh 106 has proximal mounting collar 122 fixedly attached about shaft distal end 126, and distal mounting collar 120 fixedly attached about core wire 104 near distal end 134. Proximal and distal mounting collars 122 and 120 are formed by ends of mesh 106 that are tapered or necked-down. Movement of tubular shaft 102 distally over core wire 104 causes ends of mesh 106 to move closer to each other and vice versa.

Filaments 114 of braided mesh 106 may be made from any biocompatible material known in the art. For example, mesh 106 may be constructed of stainless steel, age hardenable Nickel-Cobalt base alloy, shape-memory alloys such as nitinol, or thermoplastic or thermoset polymers. A braiding wire filament having enhanced radiopacity may also be used, and in general is made of, or coated with, a radiopaque metal such as gold, platinum, tungsten, alloys thereof, or other biocompatible metals. Suitable metals have a relatively high X-ray attenuation coefficient compared with stainless steel or nitinol so that the location of mesh 106 within the patient may be easily tracked under fluoroscopy. In addition, drawn-filed tubing (DFT) wires may be used, wherein either an outer case or an inner core of the DFT wire is made from a radiopaque material.

Figure 5:
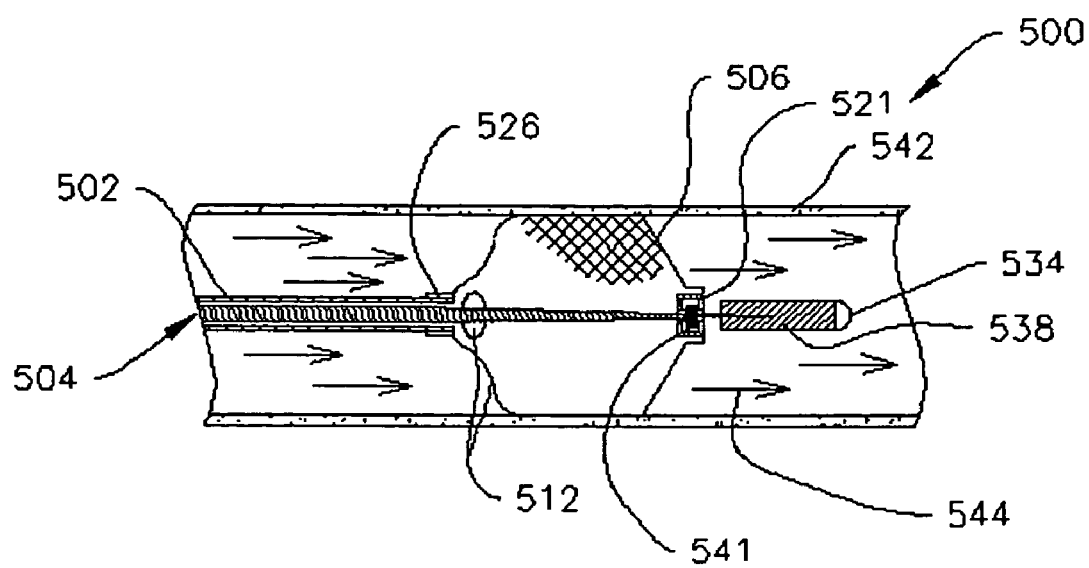
FIG. 5 is a longitudinal cross-sectional view of another embodiment of the distal protection device in a filter configuration.

The method of attaching mesh 106 to shaft 102 and core wire 104 is selected for the chosen materials, but such methods will generally include soldering, adhesive bonding, or laser welding. As shown, mesh 106 includes collars 122, 120 that are attached directly to shaft 102 and core wire 104, respectively. Alternatively, collars 122, 120 may be surrounded for reinforcement, such as with a metal or polymeric band, or a sleeve made of shrink tubing, as shown in FIG. 5. Although mesh 106 is shown attached to the outer surface of shaft 102, mesh 106 may, alternatively, be butt-joined or attached to the inner surface at shaft distal end 126.

FIG. 1 illustrates braided mesh 106 in a collapsed configuration wherein mesh 106 is collapsed about core wire 104 and has an outer diameter that is close in size to the outer diameter of shaft 102. The low profile of the collapsed configuration allows distal protection device 100 to be navigated through blood vessels with minimal obstruction of blood flow.

Figure 2:
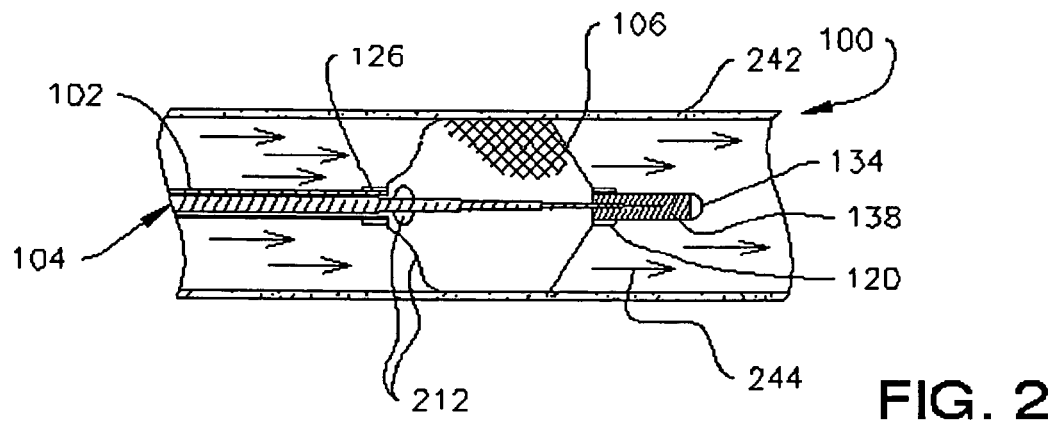
FIG. 2 is a longitudinal cross-sectional view of the distal protection device of FIG. 1 in a filter configuration.

Braided mesh 106 is radially expandable from the collapsed configuration shown in FIG. 1 to an intermediate or filter configuration wherein a portion of mesh 106 is in apposition to vessel wall 242 as shown in FIG. 2. As shown in FIGS. 1-4, a proximal portion of mesh 106 includes one or more proximal inlets 212 that admit potentially contaminated blood into the interior of mesh 106. Mesh 106 is designed so that, in the filter configuration, pores 116 are small enough to trap or filter particulate debris while allowing blood and smaller blood components to flow there through, as indicated in FIG. 2 by blood flow arrows 244.

Figure 3:
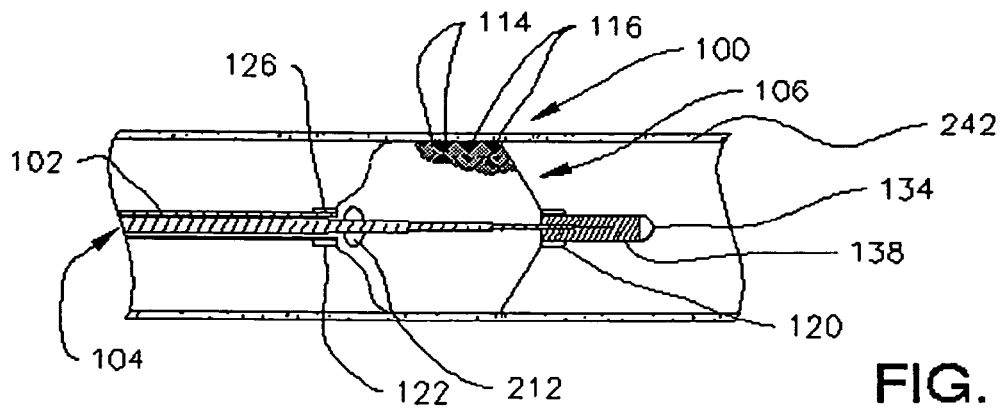
FIG. 3 is a longitudinal cross-sectional view of the distal protection device of FIG. 1 in an occlusive configuration.
Figure 4:
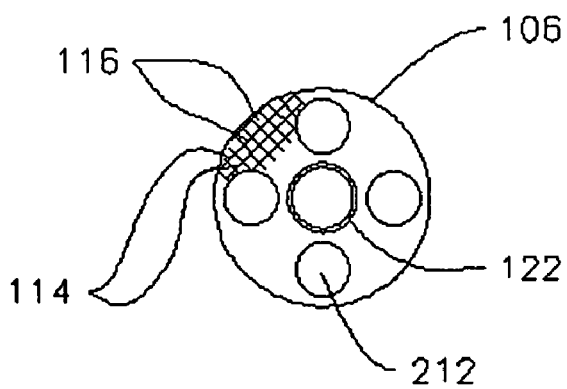
FIG. 4 is an end view of a proximal end of the distal protection device of FIG. 1 in a filter configuration.

Braided mesh 106 is longitudinally contractible from the filter configuration shown in FIG. 2 to an occlusive configuration shown in FIG. 3. To avoid having particulate debris escape or bypass distal protection device 100, mesh 106 remains in apposition with the vessel wall in the filter configuration, in the occlusive configuration, and during the transition there between. The longitudinal contraction of mesh 106 causes pores 116 to transform from a typically square shape in the filter configuration to a more diamond or rhomboid shape in the occlusive configuration. In the occlusive configuration, the reduced transverse dimensions of diamond-shaped pores 116 prevent passage of relatively smaller particles, and may nearly or completely block the flow of blood, as indicated by the absence of blood flow arrows in FIG. 3.

During use, braided mesh 106 is typically in the collapsed configuration while distal protection device 100 is introduced and located in a vessel, and during later removal from the vessel. Mesh 106 may be progressively transformed from the collapsed configuration to the filter configuration and then, if desired, to the occlusive configuration by sliding shaft 102 distally with respect to core wire 104 such that the distal ends of each component are moved towards each other, causing longitudinal contraction of mesh 106. The relative movement of shaft 102 and core wire 104 in the opposite direction progressively transforms mesh from the occlusive configuration to the filter configuration and then to the collapsed configuration. By manipulation of the relative positions of shaft 102 and core wire 104, a clinician may selectively convert mesh 106 back and forth between the filter configuration and the occlusive configuration without loosing wall apposition. When mesh 106 is in either the filter or occlusive configuration, it may be aspirated to remove any embolic particles that have been trapped therein.

FIG. 5 illustrates another embodiment of the invention in distal protection device 500, including elongate tubular shaft 502, core wire 504 and a protection element comprising braided tubular mesh 506. Distal protection device 500 has a construction similar to distal protection device 100 described above. As such, device 500 includes mesh 506 constructed from filaments 514 wherein the braided material has proximal inlets 512 and a plurality of pores 516. Mesh proximal mounting collar 523 is fixedly attached about outer surface 530 of shaft distal end 526. Core wire 504 is slidably disposed through shaft 502. Distal end 534 of wire 504 includes a flexible tip 538. FIG. 5 shows mesh 506 in a filter configuration with a portion of mesh 506 in apposition to vessel wall 542.

As distinguished from the construction of distal protection device 100, the distal end of mesh 506 is rotatably attached about core wire 504 near core wire distal end 534. Mesh 506 includes distal mounting collar 521 rotatably mounted about disc 541, which is fixedly mounted about core wire 504. Disc 541 prevents distal mounting collar 521 from sliding proximally along core wire 504. Optionally, disc 541 can also prevent distal mounting collar 521 from sliding distally along core wire 504. In distal protection device 500, core wire 504 rotates freely within mesh 506, thus enabling core wire 504 to operate as a conventional steerable guidewire to steer the device. The materials for the components of distal protection device 500 may be the same to those previously described.

Figure 6:
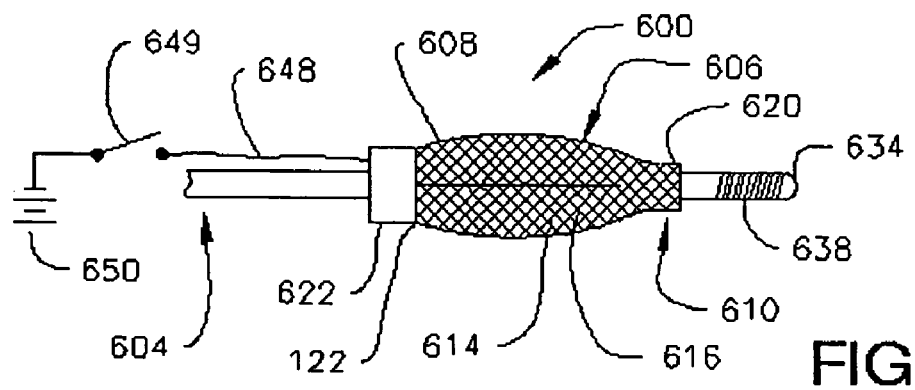
FIG. 6 is a side view of another embodiment of a distal protection device in a collapsed configuration.
Figure 7:
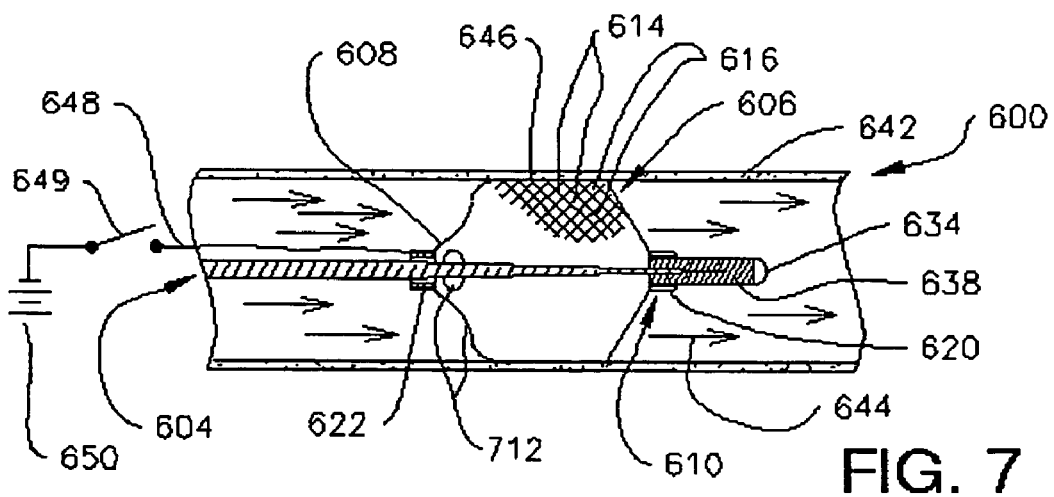
FIG. 7 is a longitudinal cross-sectional view of the distal protection device of FIG. 6 in a filter configuration.
Figure 8:
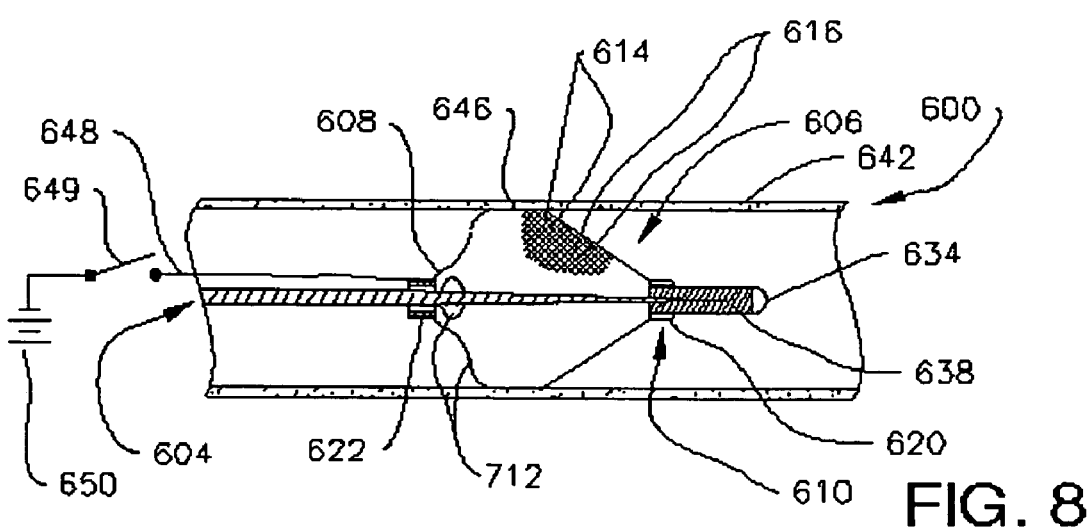
FIG. 8 is a longitudinal cross-sectional view of the distal protection device of FIG. 6 in an occlusive configuration.

Another embodiment of the distal protection device is shown in FIGS. 6-8. Like the embodiments described above, distal protection device 600 includes an elongate tubular shaft (omitted for clarity), core wire 604 having flexible tip 638 on distal end 634, and a protection element comprising braided mesh 606. Mesh 606 includes proximal mounting collar 622 fixedly attached about shaft 602, distal mounting collar 620 fixedly attached about core wire 604, at least one proximal inlet 712, and a plurality of pores 616. Inlets 712 and pores 616 allow blood to perfuse through mesh 606 when it is in a filter configuration as indicated in FIG. 7 by blood flow arrows 644. Rather than requiring relative movement between shaft 602 and wire 604 to transition mesh 606 between the collapsed, filter and occlusive configurations, mesh 606 is constructed from a thermal shape-memory alloy, and the thermal shape-memory characteristics are utilized to perform at least a portion of the transition.

As is well known in the art, components made of alloys having thermal shape-memory properties are capable of transforming from one shape to another simply by increasing the temperature of the component. For example, when nitinol is used, a component may be shaped and heat-treated so that it has a memorized shape when the material is in an austenite phase. After cooling, the material transforms into a martensite phase wherein the material can be deformed so that it retains a different shape. When the temperature of the material is increased to the austenite finish temperature $A_f$ (i.e., the temperature at which the transformation from martensite to austenite finishes upon heating) for the particular grade of nitinol, the material returns to the austenite phase and the component will tend to return to the memorized shape.

The grade of nitinol may be selected to give mesh 606 a particular austenite finish temperature $A_f$. In addition, it should be understood that a mesh incorporating different grades of nitinol may be created that is capable of transforming between different configurations at different temperatures. The grade of nitinol is selected so that the austenite finish temperature $A_f$ is generally above body temperature. Having the transition temperature above body temperature allows collapsed mesh 606 to be exposed to the body without causing the mesh to fully transform into either the filter or occlusive configurations, which might hinder its navigation through the vasculature. Some transformation may be acceptable at body temperature if it does not hinder the maneuverability of the distal protection device 600.

One process of shaping braided mesh 606 includes shaping and heat-treating mesh 606 in an occlusive configuration while the material is in an austenite phase so that the occlusive shape is memorized. After cooling the material into the martensite phase, mesh 606 can be mechanically deformed so that it retains a filter configuration. At this point, mesh 606 has both the mechanical shape memory of the filter configuration and the thermal shape memory of the occlusive configuration.

Tubular shaft 602 can then be used, as described with respect to the above embodiments, to elastically transform mesh 606 from the filter configuration to a collapsed configuration so that distal protection device 600 can be introduced into, and navigated through the patient's vasculature. Upon locating mesh 606 at a target site within a vessel, releasing shaft 602 to slide freely over core wire 604 allows mesh 606 to elastically return to the filter configuration. Then, upon heating mesh 606 above the austenite finish temperature $A_f$, mesh 606 will thermally transform to the memorized occlusive configuration. It should be appreciated that this procedure exemplifies one possible forming procedure and that the thermal shape-memory configuration is not limited to the occlusive configuration.

Since the thermal shape-memory characteristics of the mesh material are utilized for transforming the mesh between different configurations, a system is required for heating braided mesh 606 to at least the austenite finish temperature $A_f$. In the present embodiment, resistive heating is utilized. Electric lead 648 extends from external electric power supply 650 to mesh proximal end 608, and is interrupted by switch, or controller 649. Core wire 604 comprises an electrically conductive material and is connected, at its proximal end, to a ground terminal of power supply 650. The connection between core wire 604 and mesh distal end 610 completes an electric heating circuit. The circuit may be used to run electric current through thermal shape-memory filaments 614, which may act as resistive self-heating elements in mesh 606.

Alternatively, at least one resistive heating filament 646 may be interposed with thermal shape-memory filaments 614 in mesh 606. Electric current flowing through heating filament 646 will increase the temperature of filament 646 and, by thermal radiation and/or conduction, will increase the temperature of adjacent thermal shape-memory filaments 614 in mesh 606.

Alternatively, a second electric lead (not shown) may be electrically coupled to mesh distal end 610 to complete the heating circuit. In such an embodiment, core wire 604 and shaft 602 may be electrically insulated from mesh 606. As a further alternative, shaft 602 may be made from a conductive material and may substitute for either electric lead 648 or the second electric lead. An electric lead may also be incorporated, or embedded, into the wall of a non-conductive shaft 602. As a still further alternative, shaft 602 and core wire 604 may substitute for both electrical leads. In such a configuration, an insulative material may be included on an inner surface of tubular shaft 602 and/or an outer surface of core wire 604 to avoid a short circuit there between.

A portion of mesh 606 may be coated with an electrically and/or thermally insulative biocompatible material to protect apposed vessel wall 642 from electrical current passed through mesh 606, or from the temporarily elevated temperature of mesh 606. Examples of such materials include silicone, fluoropolymer or ceramic.

FIGS. 9-12 show another embodiment of the distal protection device. Distal protection device 900 has a construction similar to the distal protection devices described above, including elongate tubular shaft 902 and core wire 904 slidable there through, and distally-mounted protection element 905 capable of transforming between a collapsed configuration, a filter configuration, and an occlusive configuration. Protection element 905 includes mesh 906 braided with filaments 914 to define proximal inlets 912 and a plurality of pores 916, mesh proximal mounting collar 922 fixedly attached about shaft distal end 926, and distal mounting collar 920 fixedly attached about core wire distal end 934. Protection element 905 also includes occlusion valve 952 located within mesh 906, and expander 958 fixed to core wire 904 and being capable of forcing occlusive valve 952 into a sealing arrangement that blocks blood flow through inlets 912, as will be described below.

Figure 10:
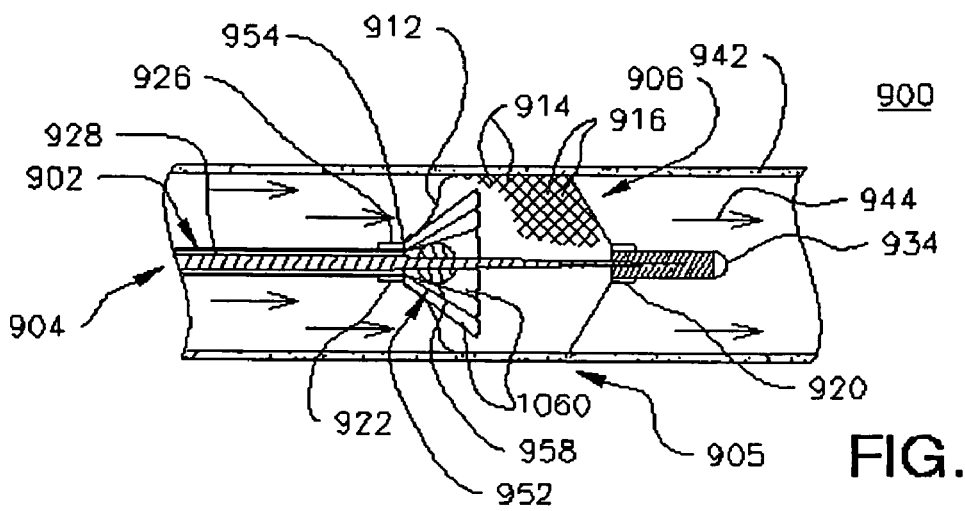
FIG. 10 is a longitudinal cross-sectional view of the distal protection device of FIG. 9 in a filter configuration.

FIG. 10 shows protection element 905 in the filter configuration, wherein blood enters inlets 912 and exits through pores 916, as indicated by blood flow arrows 944. Particulate debris larger than the size of pores 916 is trapped within mesh 906. In the filter configuration, a portion of mesh 906 is placed in apposition to vessel wall 942 so that all blood flowing in the vessel passes through mesh 906.

Figure 9:
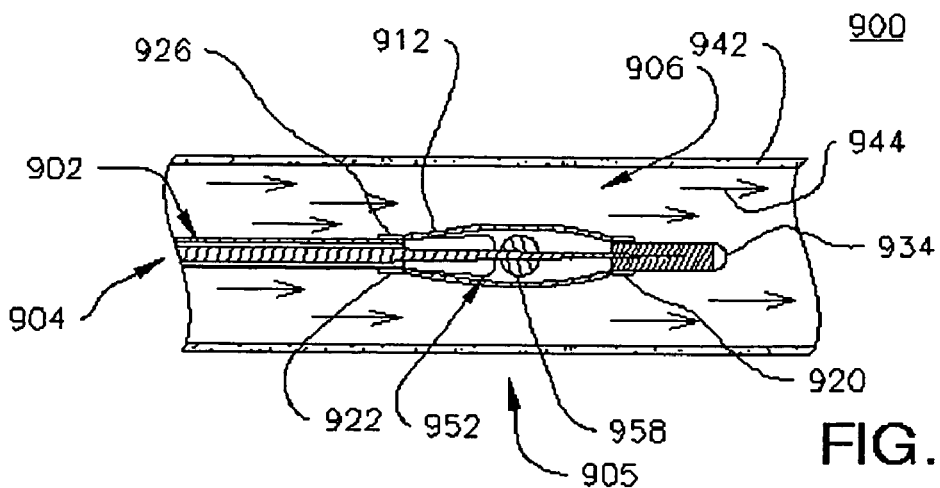
FIG. 9 is a longitudinal cross-sectional view of another embodiment of a distal protection device in a collapsed configuration.

Occlusion valve 952 includes a plurality of overlapping blades 1060 joined at valve proximal end 954. Valve proximal end 954 may be coupled to mesh 906 adjacent proximal mounting collar 922, or sandwiched between proximal mounting collar 922 and shaft distal end 926, or attached within shaft distal end 926. FIG. 9 illustrates protection element 905 in the collapsed configuration wherein blades 1060 are generally overlapped and compressed against core wire 904.

Figure 12:
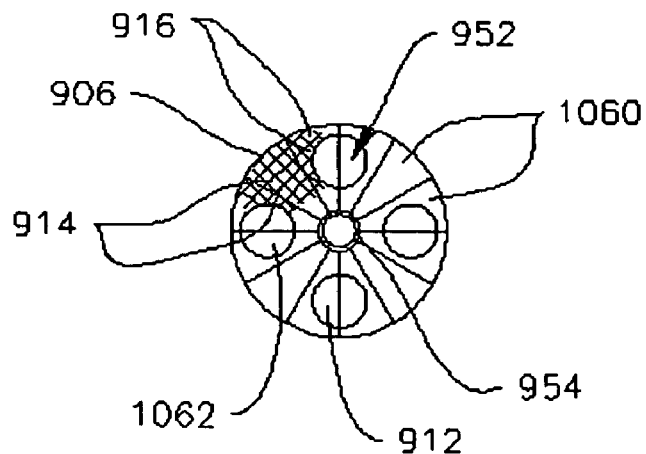
FIG. 12 is an end view of a proximal end of the distal protection device of FIG. 9 in an occlusive configuration.
Figure 11:
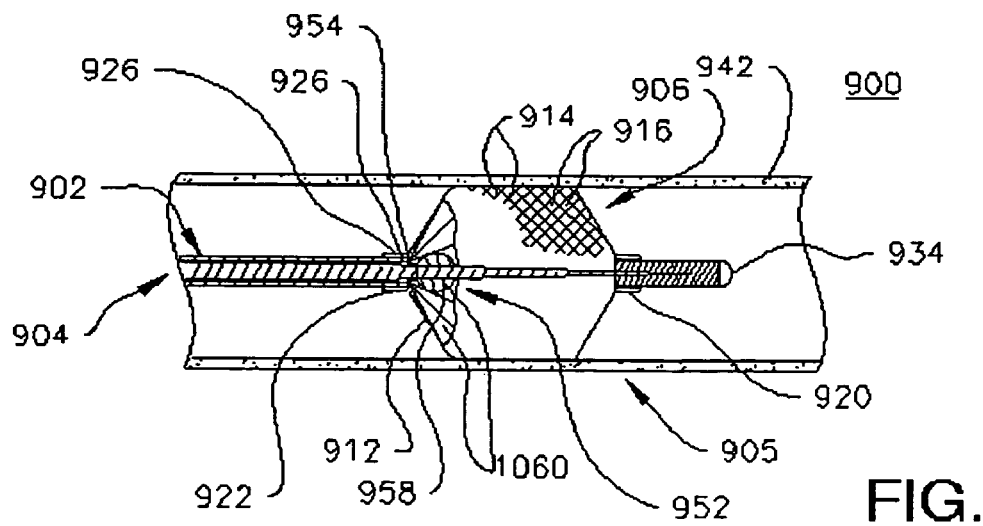
FIG. 11 is a longitudinal cross-sectional view of the distal protection device of FIG. 9 in an occlusive configuration.

FIGS. 11 and 12 show protection element 905 in the occlusion configuration wherein occlusion valve 952 is elastically deformed by expander 958 such that blades 1060 extend radially outward from valve proximal end 954 to cover inlets 912. In the optional embodiment illustrated, blades 1060 remain overlapped with adjacent blades 1060 to form an occlusive disc. Blades 1060 may be elastically bent or flexed away from valve proximal end 954 to transform between the collapsed configuration and the occlusive configuration, as follows.

FIGS. 9-11 illustrate the transition of protection element 905 between the collapsed configuration, the filter configuration and the occlusive configuration responsive to relative movement between shaft 902 and core wire 904. Similar to distal protection device 100, relative movement between shaft 902 and core wire 904 causes mesh 906 to radially expand into apposition with vessel wall 942. Simultaneously, expander 958 slides proximally within blades 1060, causing them to deform away from wire 904. FIG. 10 shows protection element 905 in the filter configuration wherein occlusion valve 952 is only partially deformed and blood flow through inlets 912 is not obstructed.

Additional relative movement between shaft 902 and wire 904 drives expander 958 deeper within occlusion valve 952 until blades 1060 are deformed into sealing engagement with inlets 912 to form the occlusive configuration as shown in FIGS. 11 and 12. FIG. 12, in particular, shows overlapped blades 1060 covering inlets 912 when occlusion valve 952 is in the occlusive configuration. In this configuration, blood is substantially blocked from passing through inlets 912. Optionally, occlusion valve 952 may include just one blade where only one inlet is included in the filter, although it should be appreciated that the number of blades need not correspond to the number of inlets.

Although relative movement between shaft 902 and wire 904 moves the ends of mesh 906 closer together, thus reducing the size of pores 916, it is occlusion valve 952 that substantially obstructs blood flow through protection element 905 in distal protection device 900. The flexibility of blades 1060, especially near valve proximal end 954, allows occlusion valve 952 to be reversibly deformed between the collapsed configuration, the filter configuration and the occlusive configuration responsive to relative longitudinal movement between shaft 902 and core wire 904. As an alternative, occlusion valve 952 may be integrally formed from a cone that includes a plurality of slits that define blades 1060. The blades would be oriented so that the blades block at least the inlets in the mesh when the occlusion valve is in the occlusive configuration.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A distal protection device comprising:
    an elongate core wire;
    an elongate tubular shaft slidably disposed about the core wire; and
    a protection element including a braided tubular mesh having a plurality of pores having transverse dimensions, wherein each pore of the mesh is selectively transformable between a filter configuration and an occlusive configuration, the mesh having at least one inlet opening adjacent a mesh proximal end, the mesh being mounted coaxially about the core wire such that a mesh distal end is coupled about a core wire distal end and the mesh proximal end is coupled about a shaft distal end;
    wherein, relative longitudinal movement between the proximal and distal ends of the mesh end causes transformation of the protection element between a collapsed configuration, the filter configuration wherein each pore of the mesh is substantially open and the occlusive configuration wherein the mesh is longitudinally contracted to reduce the transverse dimensions of the plurality of pores such that each pore of the mesh is substantially closed.

2. The distal protection device according to claim 1, wherein relative longitudinal movement between the proximal and distal ends of the mesh operatively corresponds to relative longitudinal movement between the shaft and the core wire.

3. The distal protection device according to claim 1, wherein the mesh is made of a thermal shape-memory alloy.

4. The distal protection device according to claim 3, wherein the shape-memory alloy comprises nitinol.

5. The distal protection device according to claim 3, further comprising:
    an electric power source disposed, during use, outside a patient;
    a first electric lead electrically coupled between the power source and a first location on the mesh; and
    a second electric lead electrically coupled between the power source and a second location on the mesh.

6. The distal protection device according to claim 5, wherein the core wire forms the first electric lead.

7. The distal protection device according to claim 6, further comprising insulative material disposed about the core wire.

8. The distal protection device according to claim 5, wherein the shaft forms the second electric lead.

9. The distal protection device according to claim 8, wherein the shaft is metal.

10. The distal protection device according to claim 8, wherein the shaft comprises a conductive material embedded in a polymer.

11. The distal protection device according to claim 5, further comprising an insulative coating on the mesh.

12. The distal protection device according to claim 3, further comprising a heat source interposed in the mesh and thermally coupled thereto.

13. The distal protection device according to claim 12, wherein the heat source includes at least one resistive heating element and an external electric power supply is electrically coupled thereto.

14. The distal protection device according to claim 1, wherein the core wire includes a flexible distal tip.

15. The distal protection device according to claim 1, wherein the mesh distal end is rotatably coupled about the core wire distal end.

16. A distal protection device comprising:
    an elongate core wire;
    an elongate tubular shaft slidably disposed about the core wire; and
    a protection element including a braided tubular mesh having at least one inlet for admitting blood flow into an interior of the mesh, the inlet being located adjacent a mesh proximal end, the mesh being mounted coaxially about the core wire such that a mesh distal end is coupled about a core wire distal end and the mesh proximal end is coupled about a shaft distal end;
    wherein relative longitudinal movement between the proximal and distal ends of the mesh end causes transformation of the protection element between a collapsed configuration, a filter configuration, and an occlusive configuration, and
    wherein the protection element includes a non-inflatable occlusion valve comprising a plurality of blades disposed within the mesh for blocking blood flow into the interior of the mesh via the at least one inlet when the protection element is in the occlusive configuration.

17. The distal protection device according to claim 16, wherein the occlusion valve further comprises:
    the plurality of blades having flexible proximal ends coupled adjacent the mesh proximal end, the plurality of blades being radially arranged and overlapping each other to seal against the at least one inlet when the protection element is in the occlusive configuration, the plurality of blades being disposed closely about the core wire when the protection element is in the collapsed configuration; and an expander fixed to the core wire within the mesh such that, when the core wire is drawn proximally into the shaft, the expander deforms the plurality of blades into the occlusive configuration.

18. A method of using a distal protection device comprising the steps of:

providing a distal protection device including an elongate core wire; a tubular shaft slidably disposed about the core wire; and an expandable, braided tubular mesh having a distal end attached about the core wire, a proximal end attached about the shaft, at least one inlet adjacent the mesh proximal end, and a plurality of pores having transverse dimensions, wherein each pore of the mesh is selectively transformable between a filtering configuration and an occlusive configuration;

locating the distal protection device within a vessel;

sliding the shaft distally relative to the core wire such that the mesh radially expands from a collapsed configuration to the filtering configuration wherein a portion of an outer surface of the mesh is placed in apposition to a vessel wall and wherein each pore of the mesh is substantially open; and sliding the shaft farther distally relative to the core wire such that the mesh contracts axially into the occlusive configuration wherein the sliding causes transverse dimensions of each pore of the mesh to be reduced such that each pore of the mesh is substantially closed.

19. The method of using a distal protection device according to claim 18, further comprising the step of:

aspirating the mesh, when in the filtering configuration, to remove trapped embolic particles.

20. The method of using a distal protection device according to claim 18, further comprising the steps of:

sliding the shaft proximally relative to the core wire such that the mesh is axially extended from the occlusive configuration into the filtering configuration;

sliding the shaft farther proximally relative to the core wire such that the mesh contracts radially from the filtering configuration into the collapsed configuration; and removing the distal protection device from the vessel.

* * * * *